United States Patent [19]

Heumann et al.

[11] Patent Number: 4,860,762
[45] Date of Patent: Aug. 29, 1989

[54] DUAL CHANNEL RESOLVER FOR REAL TIME ARRYTHMIA ANALYSIS

[75] Inventors: John M. Heumann, Loveland, Colo.; James M. Lindauer, San Francisco, Calif.

[73] Assignee: Hewlett-Packard Company, Palo Alto, Calif.

[21] Appl. No.: 298,220

[22] Filed: Jan. 12, 1989

Related U.S. Application Data

[63] Continuation of Ser. No. 206,990, Jun. 3, 1988, abandoned, which is a continuation of Ser. No. 905,821, Sep. 10, 1986, abandoned.

[51] Int. Cl.$^4$ ............................................. A61B 5/04
[52] U.S. Cl. ................................................. 128/702
[58] Field of Search ............... 128/696, 700, 702, 704, 128/705

[56] References Cited

U.S. PATENT DOCUMENTS

| | | | |
|---|---|---|---|
| 3,929,125 | 12/1975 | Barnes et al. | 128/702 |
| 4,432,375 | 2/1984 | Angel et al. | 128/702 |
| 4,583,553 | 4/1986 | Shah et al. | 128/704 |
| 4,589,420 | 5/1986 | Adams et al. | 128/702 |

Primary Examiner—Francis Jaworski
Assistant Examiner—George Manuel

[57] ABSTRACT

Apparatus for classifying beats in EKG signals from two sets of electrodes in which the respective signals are applied to different channels and the classification is derived from a simultaneous analysis of the signals provided by the two channels based on the quality of the channels and physiological factors of the signals.

7 Claims, 10 Drawing Sheets

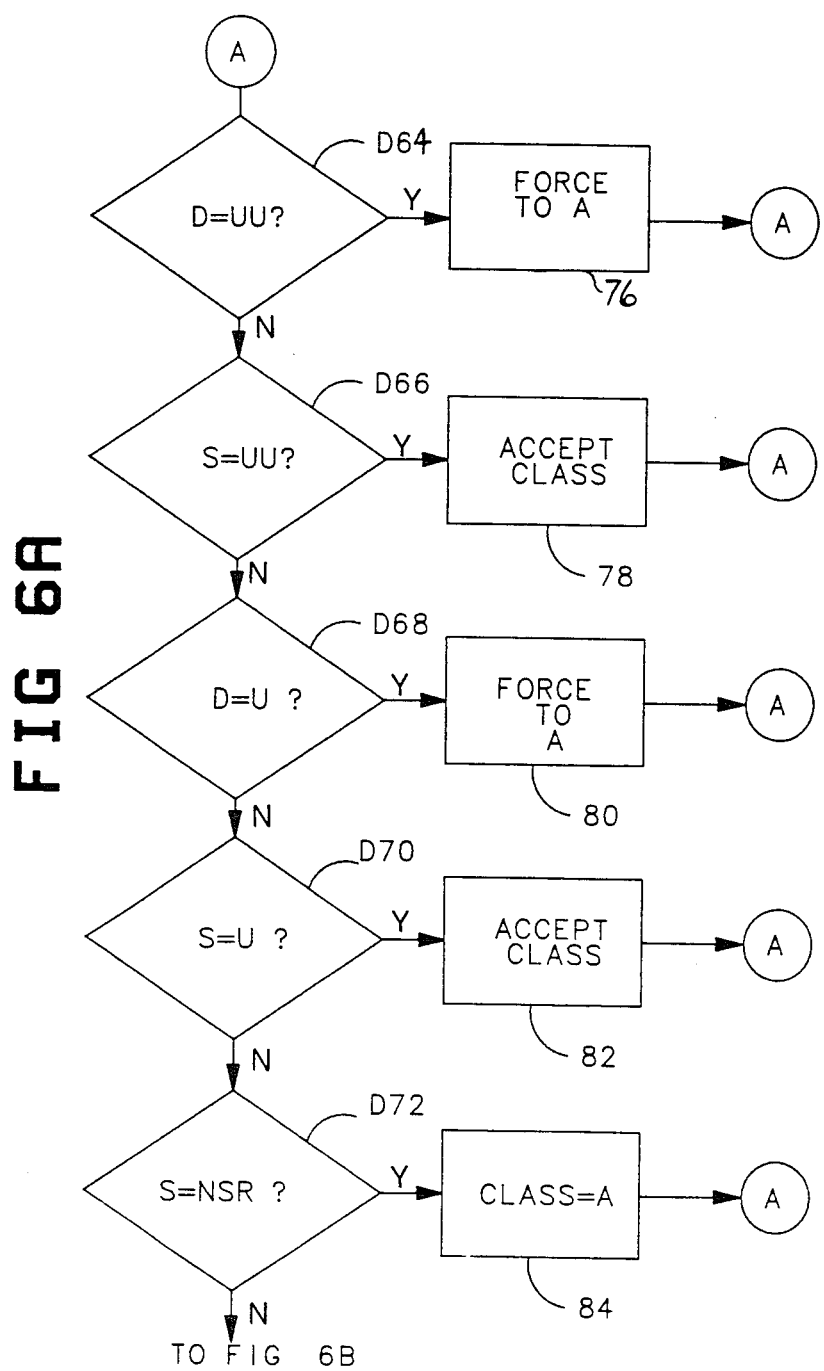

DUAL CHANNEL RESOLVER FOR REAL TIME ARRYTHMIA ANALYSIS

CROSS REFERENCE TO SELECTED APPLICATION

This application is a continuation of application Ser. No. 206,990, filed June 3, 1988, now abandoned which is a continuation of application Ser. No. 905,821, filed Sept. 10, 1986, now abandoned.

BACKGROUND OF THE INVENTION

In order to be sure of attaining all of the significant EKGs for abnormal beats of a patient's heart, it is often necessary to attain those that occur during many hours of normal activity. What is known as a Holter device is carried by the patient. It generally has two sets of electrodes that are respectively attached to different places on the patient's chest and an amplifying channel for each set. Two sets of electrodes are required for enhanced resistance to noise and sensitivity to the detection of certain events. An analyzer that classifies any beat occurring in the signals as normal, abnormal or artifact is connected to the channel having less noise. Beats that are found to be abnormal are recorded so that they can be reviewed by a physician at a later time. By connecting this analyzer to one channel or the other EKGs for abnormal beats that appear only on the other channel are missed.

BRIEF SUMMARY OF THE INVENTION

In accordance with this invention, the signals from both channels are continuously subjected to a beat by beat analysis so that there is little chance of missing beats of interest. The beats identified as abnormal are recorded. The analysis not only involves the reliability of each channel but takes into consideration certain physiological factors as well. Furthermore, this determination of channel reliability takes factors other than noise into account and may indicate whether the channel is just unreliable during this beat or is usually unreliable.

Although the simultaneous analysis of both channels could be carried out in one step, it has been found advantageous in accordance with another aspect of this invention to provide means for independently preclassifying, PC, the beats emerging from each channel and deriving a final classification, FC, with what will be called a resolver. Existing single channel algorithm have been found satisfactory for preclassifying. In most cases the use of preclassifying channels and a resolver can provide performance equal to or better than the better preclassification. Furthermore, the simultaneous analysis can readily be extended to any number of channels so that monitoring can be provided for any number of sets of electrodes.

The general procedure is as follows. If both channels are usually unreliable, a beat applied to the two channels is classified as artifact, but if one channel is usually unreliable and the other is not, the classification of the latter channel is used.

An example of a situation in which the procedure of this invention takes into account channel reliability as well as physiological information is as follows. Assume that neither channel is usually unreliable and that both are unreliable at the time when beats are applied to each. Most classification systems frequently err by classifying artifacts as abnormal beats in this situation. In order to guard against this, a final classification of abnormal will not be made even though the preliminary classification is abnormal. If both preliminary classifications are either artifact or abnormal, this beat will be considered normal if it occurs when expected from physiological considerations. Otherwise, it will be finally classified as artifact. A number of other situations occur in which the final classification is determined by channel reliability and physiological factors as well as the preliminary classifications.

The general procedure is as follows:

If neither channel is usually bad, if the beat signals applied to the channels occur within a given time window, and if the preliminary classifications provided by the channels agree, an isomorphic synchronous procedure is followed by the resolver in determining the final classification, but if the preliminary classifications do not agree, an anisomorphic synchronous procedure is followed. Should the EKG signals not occur within the time window, an asynchronous procedure is followed.

BRIEF DESCRIPTION OF THE DRAWINGS

FIGS. 6A, 6B, and 6C are a flow chart of the procedure followed when the beats are not applied to the channels within the given time window.

DETAILED DESCRIPTION OF THE INVENTION

Figure 1:
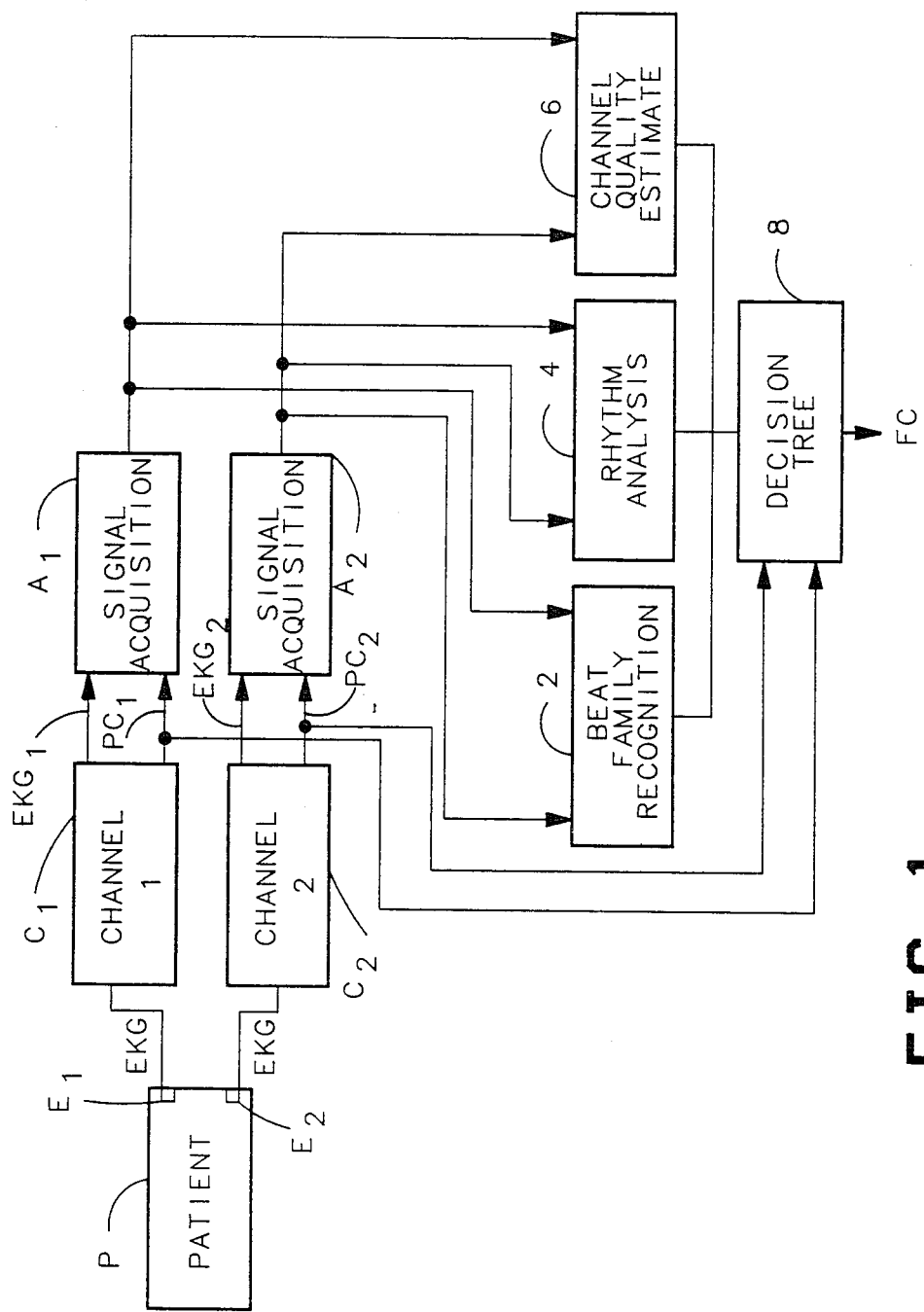
FIG. 1 is a block diagram of a beat classification system Incorporating this invention.

The pertinent technical terms are defined as follows:

Unreliable Channel—U

This terms means that a channel is unreliable at the time a beat is applied to it. Although the amount of noise in a channel could be used as the sole indication of reliability, there are situations in which this would lead to erroneous results. Therefore, it has been found advantageous to include a number of other factors, including the following:

High Frequency Noise

The amount of noise can be determined from the average amplitude of the second differences of samples of the signals. In effect this is a high pass filter.

Crowding

When three successive beats occur closer together than they would for the highest possible heart rate, the channel is considered unreliable regardless of other factors.

Sensitivity

The percentage of true beats which are detected by a channel is referred to as that channel's detection sensitivity, the numbers of true beats being those with a final classification of normal or abnormal rather than artifact.

Baseline Wander

A low pass filter can provide information as to the extent of this.

Loss of Signal

This could occur, for example, when one set of electrodes falls off.

Each of these factors is represented by a number that is multiplied by a weighting factor based on experience. Those that contribute to channel reliability are given opposite signs from those that detract from it and a sum is attained. When the sum exceeds a value based on experience, the channel is considered to be unreliable for that beat.

Usually Unreliable Channel—UU

In general, this means that a large fraction of recent beats have been unreliable. A usually unreliable channel is determined by linearly adding a given value for each beat that is determined to be unreliable by the procedure described above up to an arbitrary maximum value and subtracting a given fraction of the value so attained for each beat that is not determined to be unreliable. Whenever the value attained exceeds an arbitrary threshold, the channel is usually unreliable. Thus a usually unreliable channel is a more slowly varying index than unreliable channel.

Compensatory Pause—CP

Assume that the underlying beat rate is regular, i.e. the beats occur with an expected R—R interval X. Then if a beat is preceded by an R—R interval that is less than X and is followed by a beat with an R—R interval that is greater than X and the sum of the preceding and following R—R intervals is 2X, the beat is said to be followed by a compensatory pause. This is evidence that the beat should be considered ectopic or abnormal.

Normal Sinus Rhythm—NSR

Normal sinus rhythm is said to exist when the surrounding beats have preliminary classification, PC, of normal, the R—R intervals are reasonably constant (correspond to a heart rate of between 50 and 100 beats a minute.

Regular Rhythm—RR

Regular rhythm, RR, occurs when the pattern of the beats is understandable in terms of known physiological causes.

On Time—OT

A beat is said to be OT if it occurs when expected in the established pattern or rhythm. When the pattern is complicated, it is required that the beat not only occur when expected, but also that the physiology of the pattern or rhythm indicate that it is normal.

Recognition—REC

Recognition determines if a current beat is similar to any family of beats that have occurred. Families can be comprised of feature vectors or templates of waveforms and are updated. Comparison of the current beat with the families can be made by cross-correlation, covariance, Mahalonibis techniques or any of a number of standard pattern recognition techniques.

Before proceeding with a detailed analysis of the algorithm employed, reference is made to a system block diagram shown in FIG. 1 in which EKG signals are conducted from two pairs of electrodes E1 and E2 to the inputs of channels C1 and C2 respectively. The channels C1 and C2 respectively provide preliminary classifications PC1 and PC2 of each beat applied to their inputs. The preliminary classifications PC1 and PC2 are applied to signal acquisition means A1 and A2 respectively. The corresponding signals EKG1 and EKG2 are also respectively applied to A1 and A2. The acquired signals are applied to a means 2 for providing beat family recognition of both normal and abnormal beats for each channel, a means 4 for performing rhythm analysis of each channel and a means 6 for making an estimate of unreliable and usually unreliable i.e. quality, for each channel so that their respective reliabilities are known.

The outputs of 2, 4, and 6 for each channel are conveyed to a decision tree 8 as are the preliminary classifications PC1 and PC2. The decision tree 8 is merely one means for determining the final classification FC from the preliminary classification PC1 and PC2 and the physiological information supplied by the beat family recognition means 2, the rhythm analysis 6 and the channel quality estimating means 6.

Figure 2:
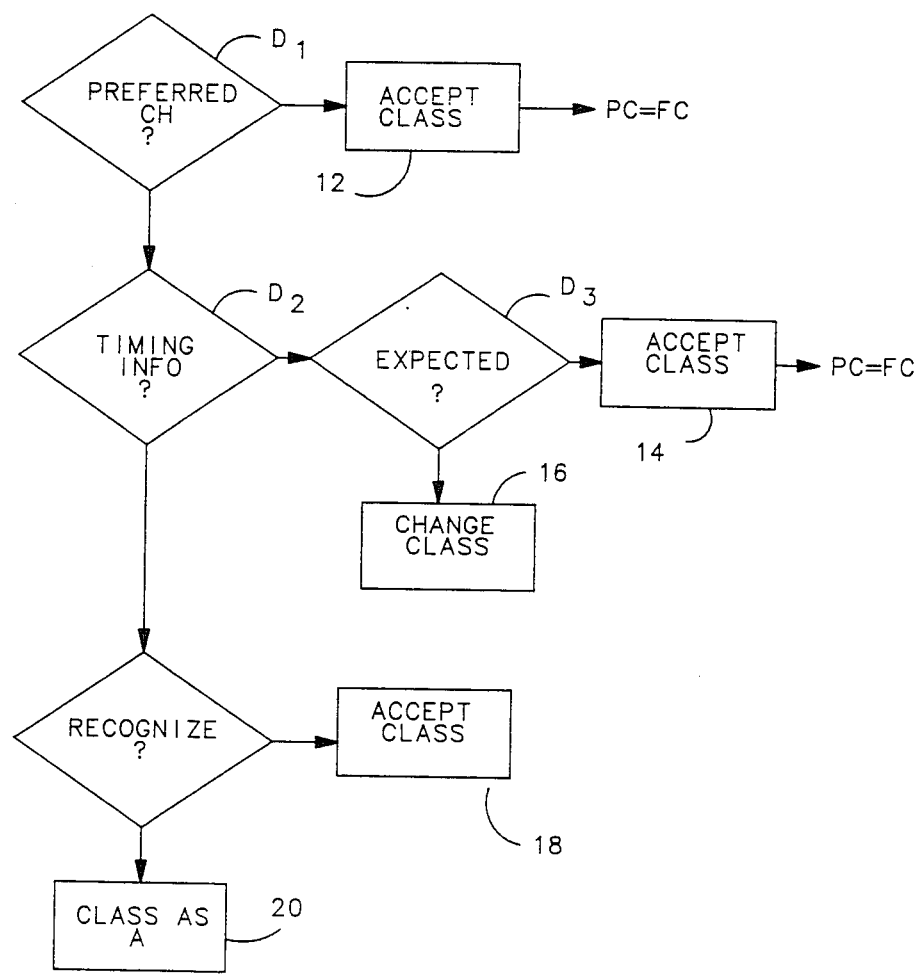
FIG. 2 is a flow chart illustrating the overall procedure used in classifying beats in accordance with this invention.

As will be clear from the detailed description of one algorithm that can be used in this invention, the general operation is as set forth in FIG. 2. If there is a preferred channel, decision block D2 determines whether a regular rhythm RR exists. If so, a decision block D3 determines whether the current beat is on time, OT. If so, the preliminary classification PC is the final classification FC, block 14, but if not, FC is different from PC, block 16. Should there be no RR, a decision block D4 determines whether the current beat is recognized. If so, the PC is accepted as FC, block 18, but if not, the beat is classified as artifact, block 20.

Figure 3:
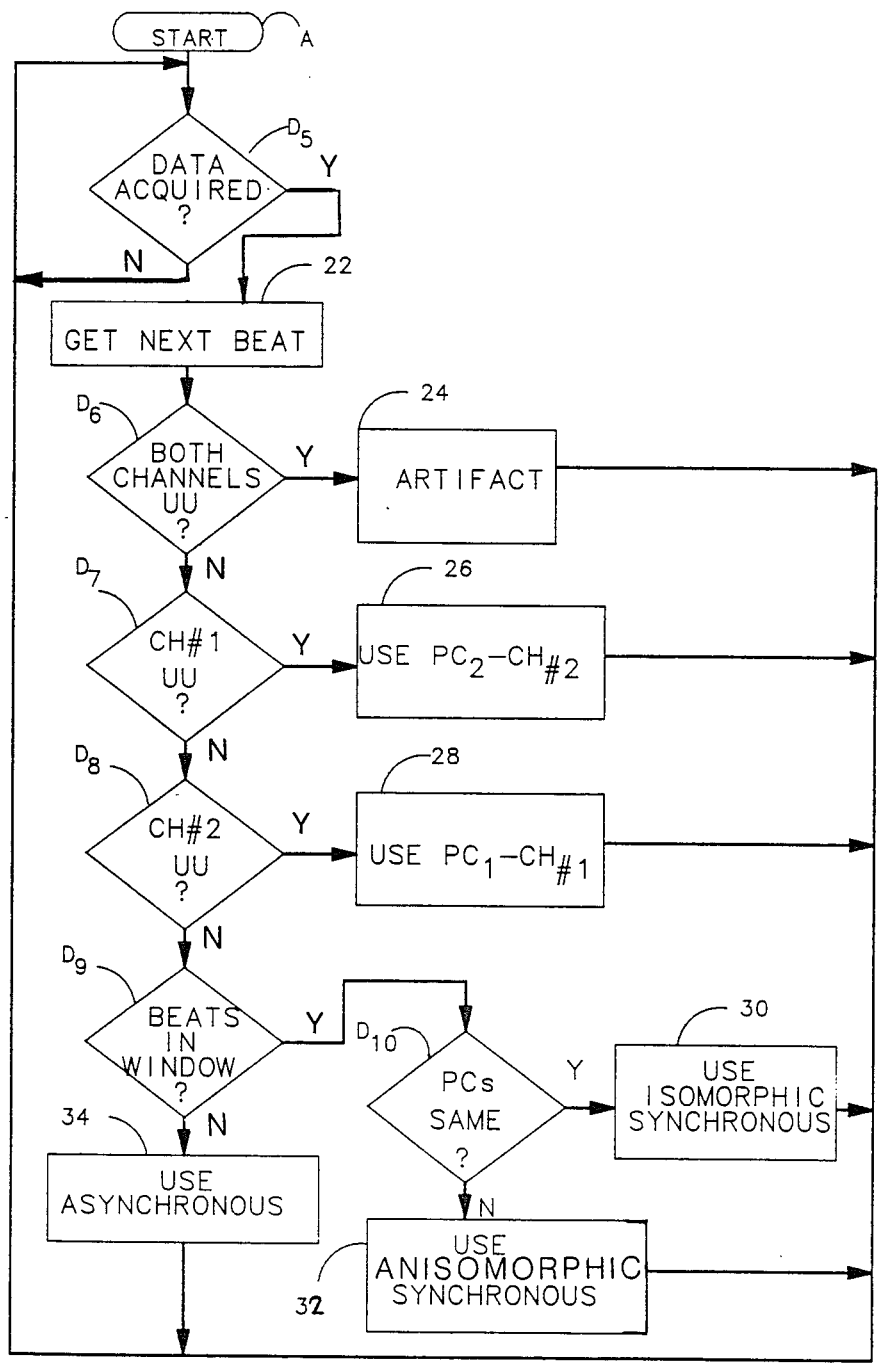
FIG. 3 is a flow chart illustrating how the main branches of the algorithm of this invention are selected.

Reference is now made to FIG. 3 for a description of the first portion of the algorithm that determines which major branch of the decision tree is to be followed. In these flow charts a true answer to a decision is horizontal and a false answer is vertical. D5 determines whether data has been acquired. If so, get next beat, block 22. D6 determines if both channels are usually unreliable, UU. If so, the beat is classified as artifact, block 24, but if not, D7 checks whether channel #1 is usually unreliable. If so, use the preliminary classification PC2 of channel #2, block 26, but if not, D8 checks to see if channel #2 is usually unreliable. If so, use preliminary classification PC1 of channel #1, Block 28, but if not D9 checks whether the beats applied to the channels occur within a time window of 160 milliseconds. If so, D10 determines whether the preliminary classifications PC1 and PC2 are the same. If they are, the isomorphic synchronous procedure is used, block 30, but if not, the anisomorphic synchronous procedure is used, block 32. On the other hand, if D9 determines that the beats are not in the time window an asynchronous procedure is used, block 34.

Isomorphic Synchronous Procedure

Figure 4:
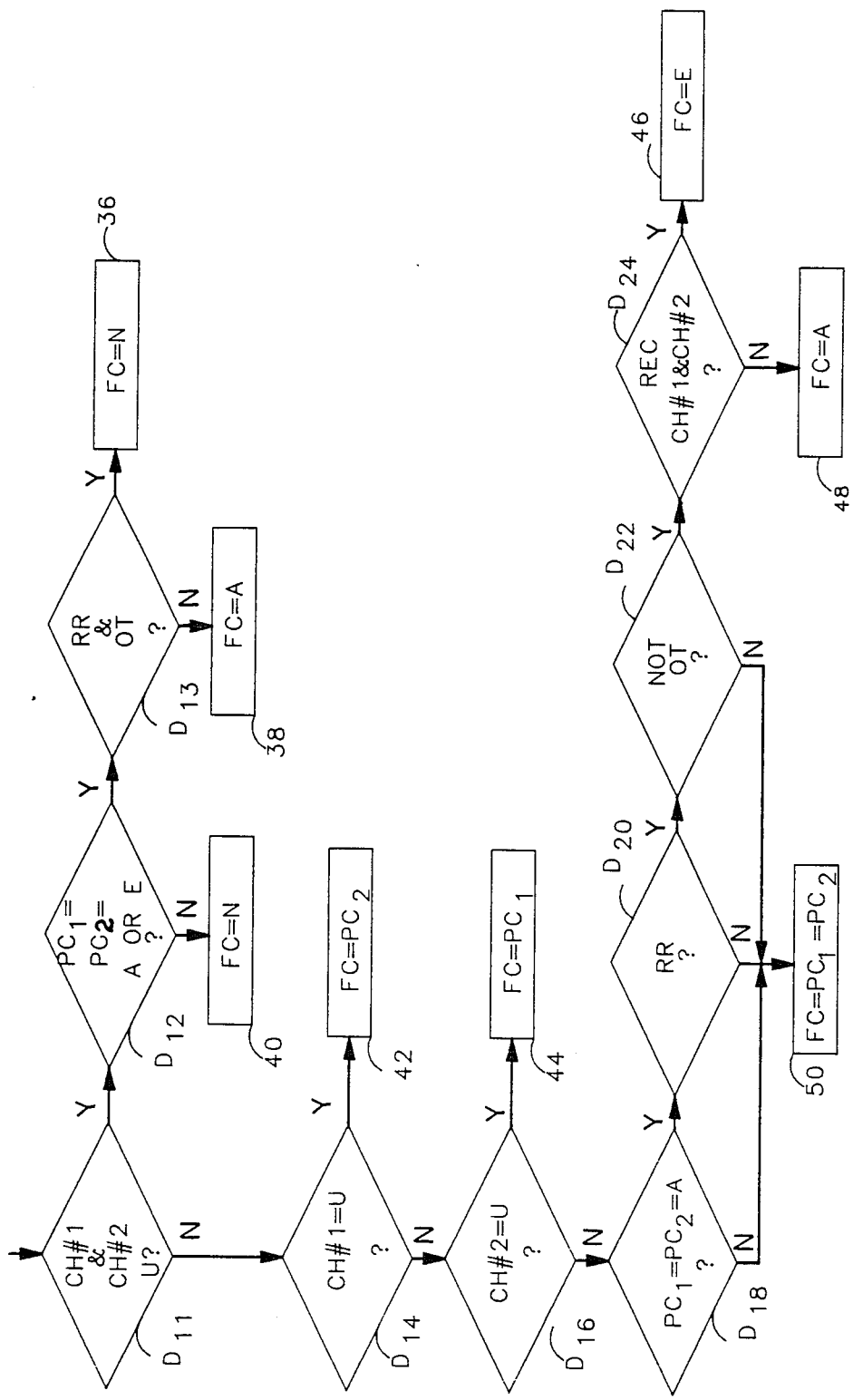
FIG. 4 is a flow chart of the procedure followed when beats are applied to the channels within a given time window and have the same preliminary classification.

This procedure is illustrated in FIG. 4 and is used when both beats occur within the time window and PC1=PC2. At this point, neither channel is usually unreliable, but if D11 indicates that both channels are unreliable for this beat, it is arbitrarily decided that the final classification FC will not be ectopic even if PC1=PC2=E. D12 determines if the preliminary classifications are A or E. If so, D13 checks to see if the beats are in R—R and OT. If they are, this physiological information suggests that they are normal beats, so that FC=N block 36, but if they are not, FC=A, block 38. On the other hand, if D12 indicates that PC1 and PC2 are not equal to A or E and therefore =N, FC=N, block 40. Thus even if PC1 =PC2 =E, physiological considerations do not permit FC=E.

If D11 indicates that both channels are not unreliable, D14 checks to see if channel #1 is unreliable. If it is FC =PC2, block 42. If D14 indicates that channel #1 is not unreliable, D16 determines whether channel #2 is unreliable. If it is, FC =PC1, block 44. Actually, since the preliminary classifications are the same, that classification is used if one channel is unreliable.

At this point the procedure relies on information as to channel quality as well as on physiological information. If neither is unreliable and D18 indicates that the preliminary classifications are artifact, there is a good possibility that the beats are ectopic if they are in regular rhythm RR and not OT, as respectfully indicated by D20 and D22. This becomes a reliable conclusion, block 46, if D24 indicates that the beats are recognized as closely resembling another ectopic beat that has been stored in memory. If there is no recognition, the preliminary classification of A is allowed to be stored, block 48, so that FC =A. But if any of D18, D20 and D22 are false, the preliminary classification is accepted as the final classification, block 50.

Anisomorphic Synchronous

Figure 5A:
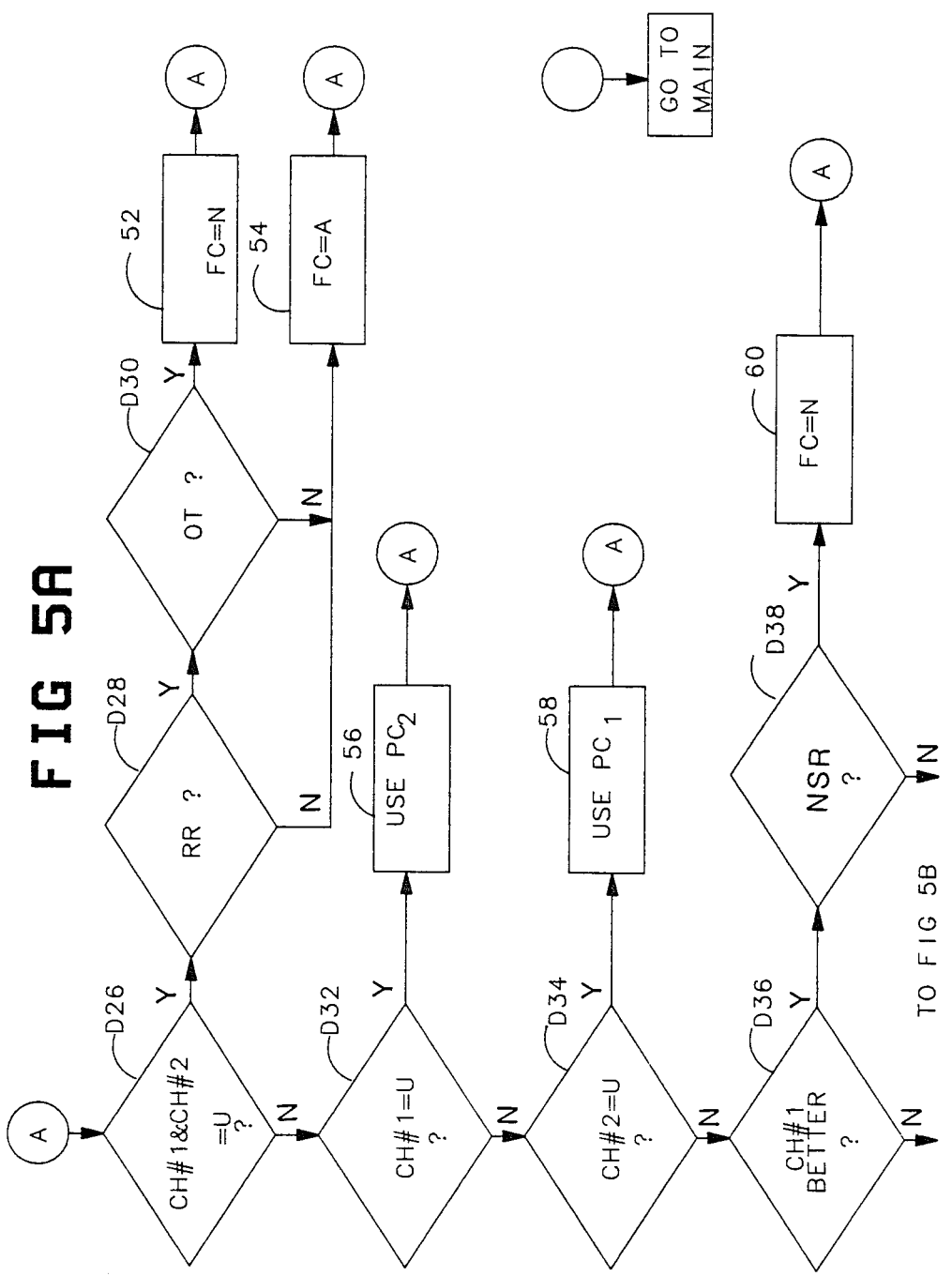
FIGS. 5A, 5B and 5C are a flow chart of the procedure followed when beats are applied to the channels within a given time window and have different preliminary classifications.
Figure 5B:
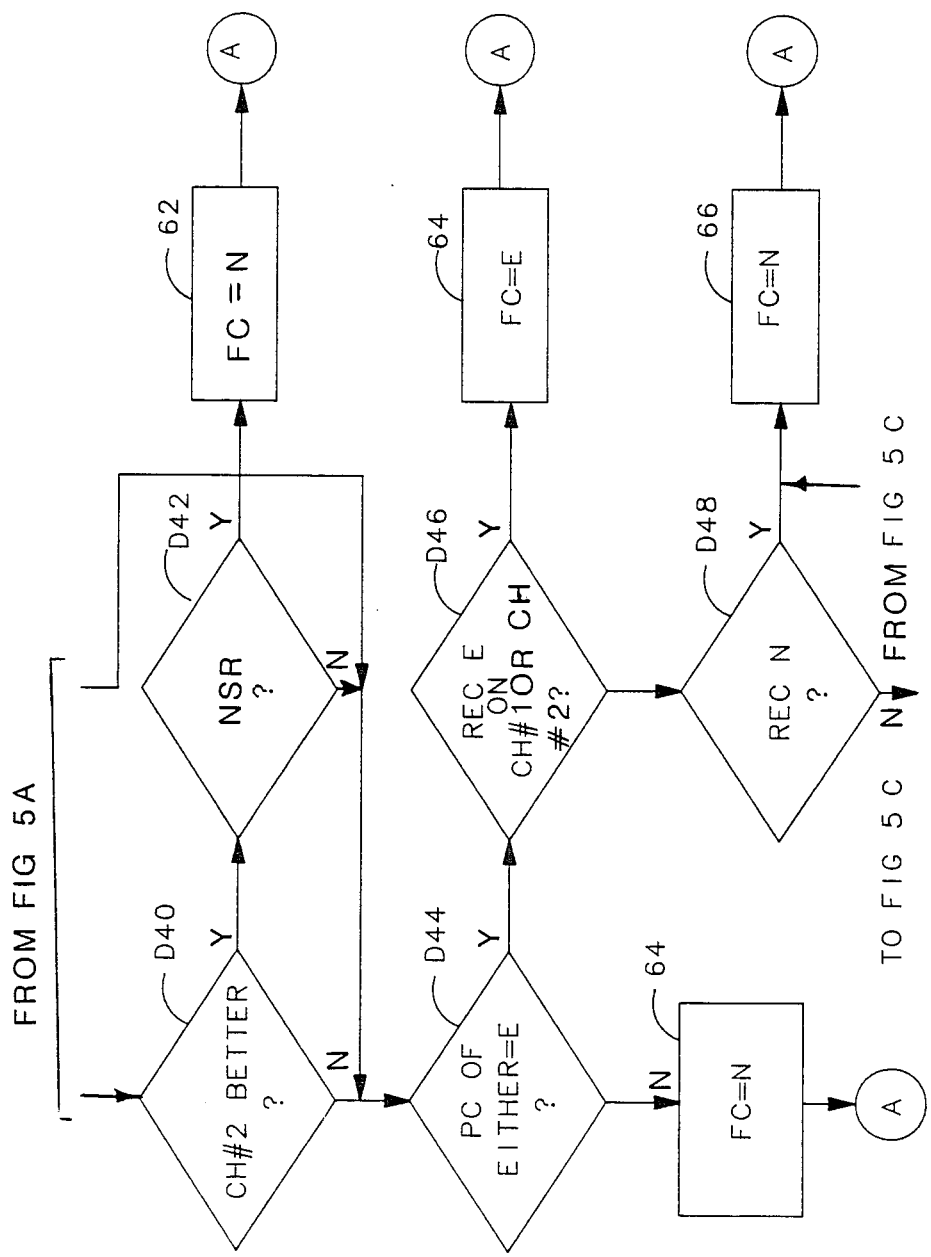
Figure 5C:
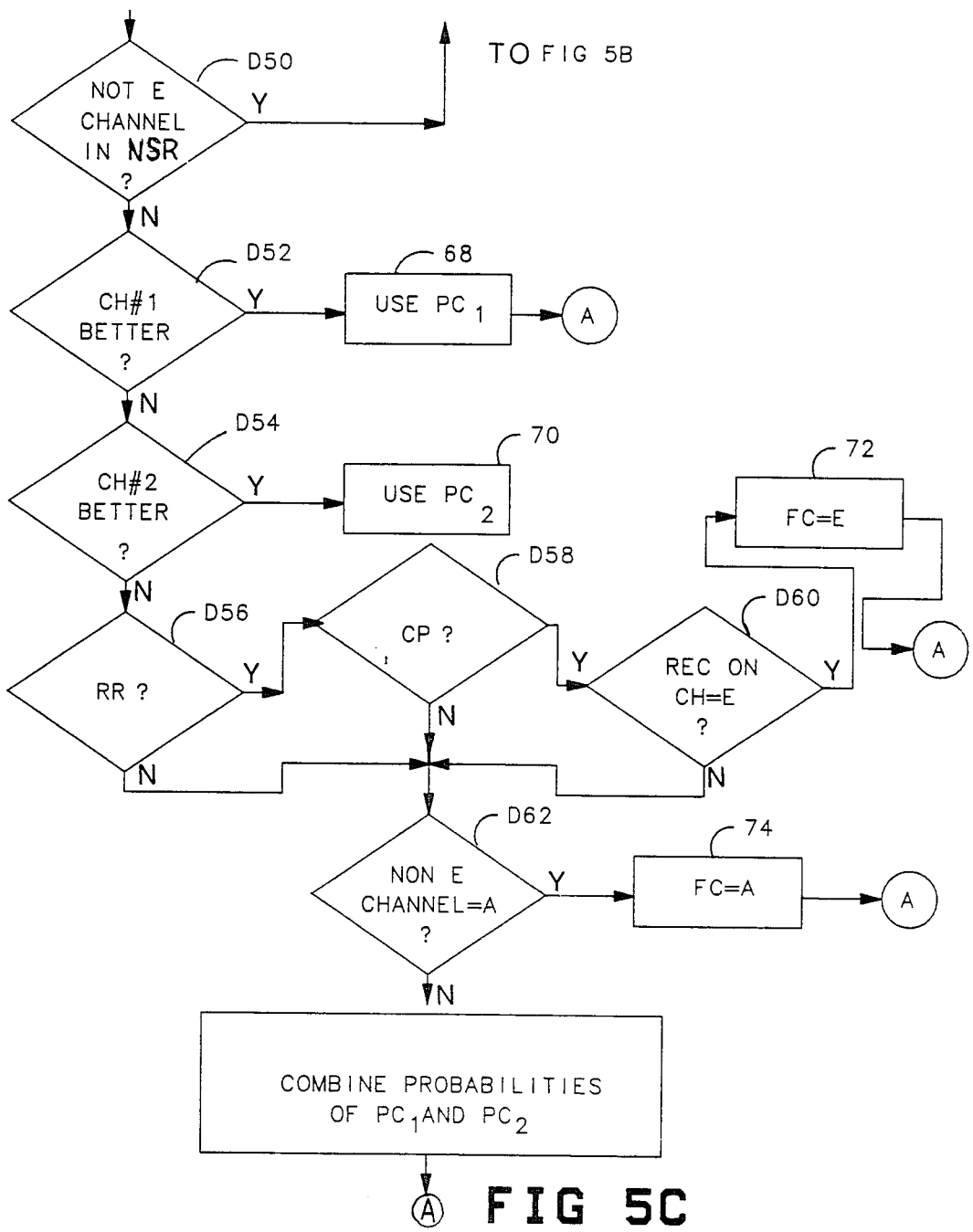

The procedure is illustrated in FIG. 5 and is followed when the beats are within the time window but have different preliminary classifications, i.e. PC1 is not equal to PC2. This is a more difficult case since the preliminary classifications of the two channels are not in agreement. Nonetheless, the fact that a beat has been detected by both channels decreases the probability of it being an artifact. As in the isomorphic synchronous case just discussed, D26 tests whether both channels are unreliable. If they are, an FC of ectopic, E, is arbitrarily ruled out and D28 and D30 respectively check for R—R and OT. If both are true, FC =N, block 52, but if either is false, the FC is forced to A, block 54.

If D26 indicates that both channels are not unreliable, D32, D34, block 56 and block 58 respectively perform the function of D14, D16, block 42 and block 44 of FIG. 4.

At this point an investigation is made to see if either channel is significantly better than the other. If one is and if there is a normal sinus rhythm, NSR, on the better channel, the final classification is made to be N regardless of what the PC of that channel is. These functions are carried out for channel #1 by D36, D38., and block 60 and by D40, D42 and block 62 for channel #2.

If there is no normal sinus rhythm or if neither channel is better than the other, D44, determines whether the PC of either channel is E. If not, the FC =N, block 64. The reason for this is that if both channels detected something and one is N there is no reason to think that the beats are other than normal.

If D44 indicates that either channel's preliminary classification is E, then the preliminary classification of the other channel will be A or N. If the beats on each channel are recognized, D46, or if they respectively match stored ectopic beats, then FC =E, block 64. If there is not a match, D48 checks to see if there is a match with the updated normal. If so, FC =N, block 66, but if not the channel having a PC =A or N is checked for normal sinus rhythm NSR by D50. If that channel is in NSR, FC =N, the block 66.

If no match is formed and there is no normal sinus rhythm, NSR, the FC=the PC of the better channel, if there is one. If D52 determines that channel 1 is better, its PC, is the FC, block 68, and if D54 determines that channel, PC2 is the FC, block 70.

If none of the above procedures result in a final classification, D56 and D58 check to see if there is a compensatory pause, and D60 checks to see if the beat is recognized as E on just the channel that has a PC of E. If so, the beat is classified as E, block 72.

If any of D56, D58, or D60 are false, and the channel that does not have a PC of E, i.e. the one that is A or N has a PC of A, the FC is A, block 74.

On the other hand, if the channel that could be A or N is N, the question of whether FC =N or E is determined by the relative probability in both channels.

Asynchronus

Figure 6B:
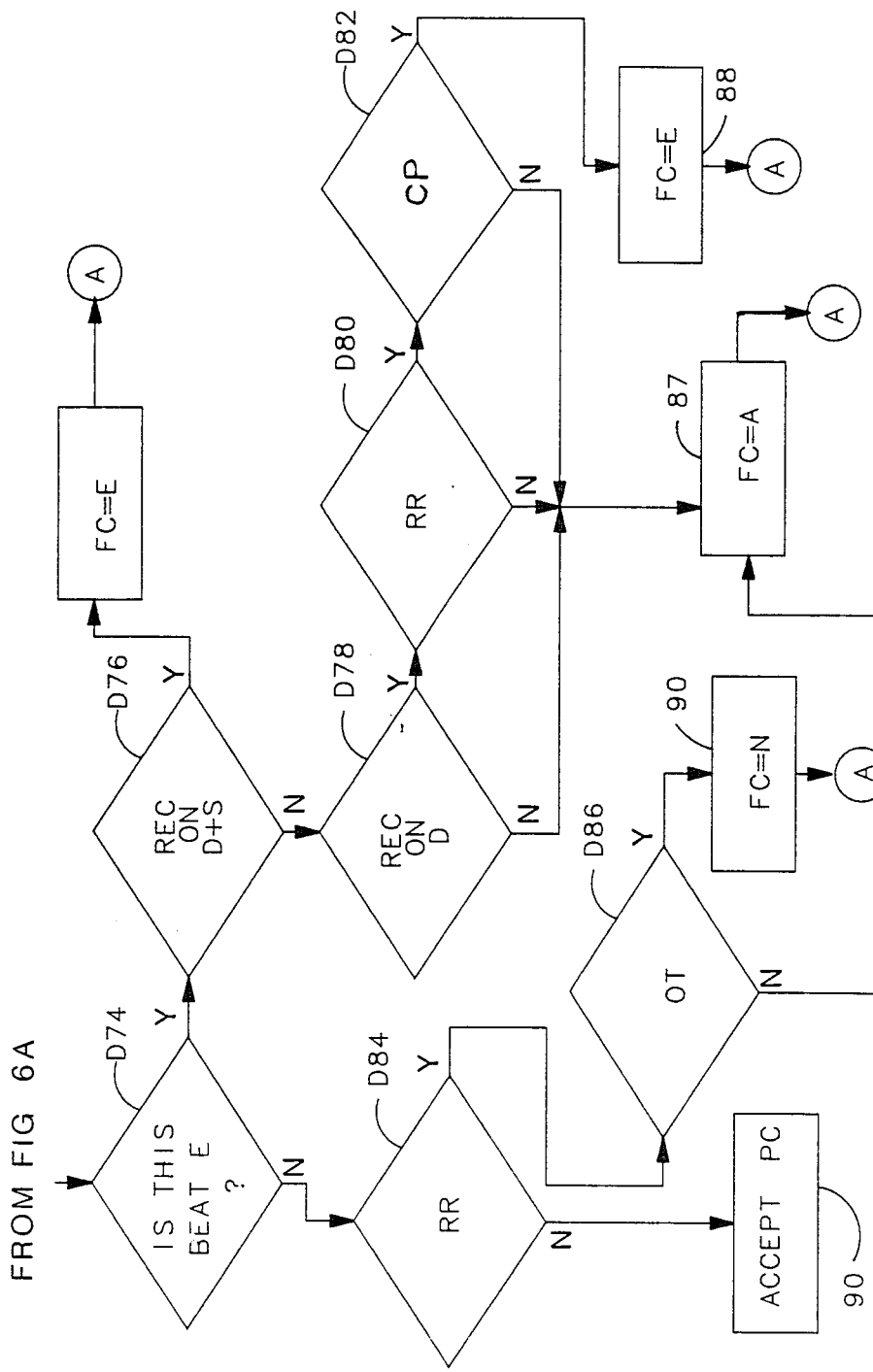

In this procedure, as illustrated in FIG. 6, the beats are not applied to the channels within the time window. The current beat to be classified is on one channel called D and the other channel on which there is no beat is called S. If the D channel has a preliminary classification of ectopic, E, corroborating evidence is derived from recognition and timing.

If D64 indicates that channel D is usually unreliable, the final classification is forced to A, block 76 regardless of what the PC of the D channel is. But if D is not usually unreliable and D66 indicates that the silent channel is usually unreliable the PC of channel D is accepted as the final classification, FC, block 78.

If neither D or S are usually unreliable, D68 checks to see if D is unreliable for this beat. If so, the final classification FC =A, block 80. If D68 indicates that channel D is not unreliable for this beat, and if D70 indicates that the S channel is unreliable for this beat, the FC =PC of the D channel, block 82.

Should D68 and D70 indicate that neither channel is unreliable for this beat and if D72 indicates that the silent channel S is in normal sinus rhythm NSR, the chances are that S is a normal channel and that D's beat is artifact so that FC is set at A, block 84.

If D72 indicates that channel S is not in NSR, D74 checks to see if the $PC_d$ is E. If so, D 76 checks to see if the beat on D and the absence of a beat on S is a recognized pattern. If so, the final classification is E, block 86. However, should D76 indicate that there is no recognition, REC, on both channels D and S, D78 checks to see if the beat on the detecting channel D is recognized. If so and if D80 and D82 respectively indicate that channel D is in RR and that there is a compensating pause, the FC =E, block 88. If any one of D78, D80 and D82 are false, the preliminary classification of the D channel, which was A is set as the FC, block 88.

On the other hand, if D74 indicate that the PC of D channel is not E and is therefore either N or A, D84 checks to see if the D channel is in RR. If so, and if D86 indicates that the beat in the D channel is OT, the FC =N, block 90. But if D86 determines that the beat is not OT, the FC=A, the block 87.

In the event that D84 indicates that the beat is not in R—R, the FC is in the $PC_d$, which may be N or A.

Figure 7:
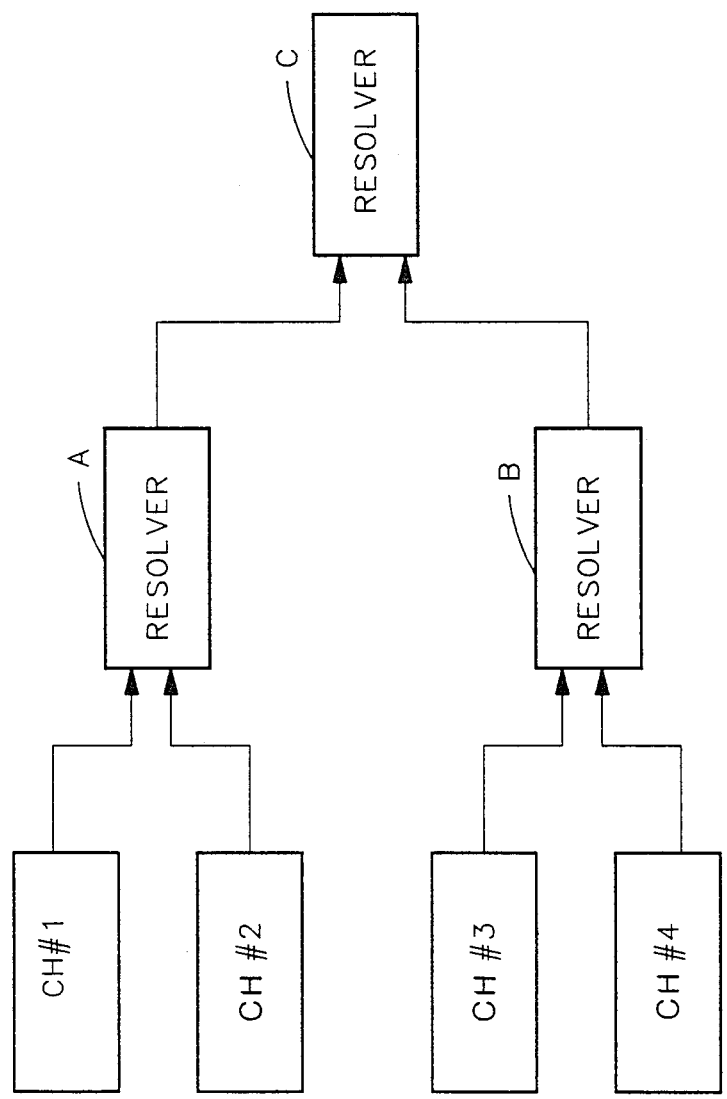
FIG. 7 is a block diagram illustrating how four channels can be used with a resolver.

If the simultaneous analysis of the beats is performed in accordance with the invention by a single algorithm, it will only be useful for the number of sets of electrodes for which the algorithm is designed, but the use of the preferred form of this invention in which preliminary classifications are made for the beats from each set of electrodes and a resolver is provided makes a final classification from two preliminary classifications and physiological information related to those beats, permits the use of any number of sets of electrodes. This advantage is illustrated in FIG. 7 in which channels #1 and #2 provide preliminary beat classifications from which a final classification is derived by a resolver A and channels #3 and #4 provide preliminary classifications from which a final classification is derived by a resolver B. The final classification derived by the resolvers A and B are treated as preliminary classifications and are applied to a resolver C that produces the true final classification.

In the determination of a final classification of a beat from its preliminary classification, as illustrated by the charts above, physiological information including synchronism, rhythm, shape and recognition of shape is used but if the attendant loss in performance is satisfactory, certain of these could be eliminated. In fact other physiological information might be used. The important thing is to make the final classification of a beat from a simultaneous analysis of the quality or reliability of two channels and physiological information related to the beat.

In the determination of a final classification from the preliminary classifications as illustrated in the flow charts above, physiological information including synchronism, rhythm, which is the existence of recognizable patterns occurring with appropriate timing (e.g. compensatory pause), shape and recognition of shape have been used. Other physiological information could be used as well but the ones enumerated have been found effective. Furthermore, some of the enumerated physiological information can be omitted if less accurate results can be tolerated.

We claim:

1. Apparatus for classifying beats in EKG signals comprising:
   a first channel to which EKG signals from a first set of electrodes may be coupled;
   a second channel to which EKG signals form a second set of electrodes may be coupled;
   the first channel including means for continuously monitoring the EKG signals from the first set of electrodes and for producing a first preliminary classification signal indicative of a preliminary classification of beats in the EKG signals from the first set of electrodes, the second channel including means for continuously monitoring the EKG signals from the second set of electrodes for producing a second preliminary classification signal indicative of a preliminary classification of beats in the EKG signals from the second set of electrodes, the first preliminary classification signal being determined independently of the EKG signals from the second set of electrodes and the second preliminary classification signal being determined independently of the EKG signals from the first set of electrodes;
   means for providing a third signal indicative of the quality of said first channel;
   means for providing a fourth signal indicative of the quality of said second channel;
   means for continuously deriving a fifth signal independently of the EKG signals applied to said second channel and indicative of at least one physiological factor of the EKG signals coupled to said first channel;
   means for continuously deriving a sixth signal independently of the EKG signals applied to said first channel and indicative of at least one physiological factor of the EKG signals coupled to said second channel; and
   analysis means responsive to said first and second preliminary classification signals and to the third, fourth, fifth and sixth signals for deriving a final classification of a beat applied to at least one of said channels.

2. Apparatus for classifying beats in EKG signals comprising:
   a first channel to which EKG signals from a first set of electrodes may be coupled, the first channel including means for monitoring the EKG signals from the first set of electrodes and for producing a first preliminary classification signal indicative of a preliminary classification of the beats in the EKG signals from the first set of electrodes;
   a second channel to which EKG signals from a second set of electrodes may be coupled, the second channel including means for monitoring the EKG signals from the second set of electrodes and for producing a second preliminary classification signal indicative of a preliminary classification of beats in the EKG signals from the second set of electrodes;
   the first and second channels monitoring the EKG signals and producing the preliminary classification signals independently of one another;
   means for providing a third signal indicative of the quality of said first channel;
   means for providing a fourth signal indicative of the quality of said second channel;
   means for deriving a fifth signal indicative of at least one physiological factor of the EKG signals applied to said first channel;
   means for deriving a sixth signal indicative of at least one physiological factor of the EKG signals applied to said second channel;
   analysis means responsive to said first and second preliminary classification signals and to the third, fourth, fifth and sixth signals for deriving a final classification of a beat applied to at least one of said channels.

3. An apparatus as set forth in claim 2 in which the fifth and sixth signals are indicative of the rhythm of beats in the EKG signals and are indicative of whether the beats are on time, the apparatus further comprising:
   means for providing a signal indicating that the EKG signals are applied to said first and second channels within a given time window;
   means for providing a signal indicating when the first and second preliminary classifications are the same; and
   the analysis means comprising a signal resolver means responsive to the EKG signals being applied within the time window and the first and second preliminary classifications being the same to provide a signal for a final classification of normal (a) when the third and fourth quality signals indicate that both channels are unreliable and both preliminary classifications are normal; and (b) when the first and second quality signals indicate that both channels are unreliable, both preliminary classifications are ectopic or artifact and the third and fourth signals representative of physiological features indicate that the rhythm of the EKG signals is regular and that beats in the EKG signals are on time.

4. An apparatus as set forth in claim 2 in which the fifth and sixth signals are indicative of the rhythm of beats in the EKG signals and wherein the beats are on time, the apparatus further comprising:
- means for providing a signal indicating that the EKG signals are applied to said first and second channels within a given time window;
- means for providing a compare signal indicating when the first and second preliminary classifications are the same;
- a memory;
- means for updating said memory with an EKG signal having a final classification of ectopic;
- means for comparing a current EKG signal with EKG signals stored in said memory; and
- the analysis means comprising a signal resolver means responsive to the compare signal for deriving a signal for a final classification of ectopic when said quality signals indicate that both channels are reliable, the fifth and sixth signals indicate that the EKG signals are in rhythm and not on time, and the means for comparing indicates that the current EKG signals match updated ectopic EKG signals stored in said memory.

5. An apparatus as set forth in claim 2 further comprising:
- means for providing a signal indicating that the EKG signals are applied to said first and second channels are within a given time window;
- means for providing a signal indicating whether the first and second preliminary classifications are the same;
- a memory;
- means for updating said memory with an EKG signal having a final classification of ectopic;
- means for comparing a current EKG signal with EKG signals stored in said memory; and
- the analysis means comprising a signal resolver that derives a signal for a final classification of ectopic when the EKG signals occur within the given time window, said third and fourth signals indicative of quality indicate that both channels are reliable and the preliminary classifications of both channels indicate that the EKG signals are ectopic.

6. Apparatus as set forth in claim 1 wherein said physiological factor is a similarity of shape.

7. Apparatus as set forth in claim 1 wherein said physiological factor is a rhythm.

* * * * *